United States Patent
Sato

(10) Patent No.: US 9,701,744 B2
(45) Date of Patent: Jul. 11, 2017

(54) ANTI-VASOHIBIN 2 ANTIBODY

(71) Applicant: TOHOKU UNIVERSITY, Sendai-shi, Miyagi (JP)

(72) Inventor: Yasufumi Sato, Sendai (JP)

(73) Assignee: TOHOKU UNIVERSITY, Sendai-Shi, Miyagi (JP)

( * ) Notice: Subject to any disclaimer, the term of this patent is extended or adjusted under 35 U.S.C. 154(b) by 274 days.

(21) Appl. No.: 14/649,091

(22) PCT Filed: Nov. 11, 2013

(86) PCT No.: PCT/JP2013/080450
§ 371 (c)(1),
(2) Date: Jul. 30, 2015

(87) PCT Pub. No.: WO2014/087810
PCT Pub. Date: Jun. 12, 2014

(65) Prior Publication Data
US 2016/0009790 A1    Jan. 14, 2016

(30) Foreign Application Priority Data

Dec. 3, 2012 (JP) ................................ 2012-264350

(51) Int. Cl.
| | | |
|---|---|---|
| C07K 16/00 | (2006.01) | |
| A61K 39/395 | (2006.01) | |
| G01N 33/53 | (2006.01) | |
| C07K 16/18 | (2006.01) | |
| C12N 5/16 | (2006.01) | |
| C07K 16/22 | (2006.01) | |
| G01N 33/574 | (2006.01) | |
| G01N 33/50 | (2006.01) | |
| G01N 33/564 | (2006.01) | |
| A61K 39/00 | (2006.01) | |

(52) U.S. Cl.
CPC .............. *C07K 16/18* (2013.01); *C07K 16/22* (2013.01); *C12N 5/163* (2013.01); *G01N 33/50* (2013.01); *G01N 33/564* (2013.01); *G01N 33/57484* (2013.01); *A61K 2039/505* (2013.01); *C07K 2317/34* (2013.01); *C07K 2317/76* (2013.01); *G01N 2500/00* (2013.01); *G01N 2500/04* (2013.01); *G01N 2800/52* (2013.01); *G01N 2800/7014* (2013.01)

(58) Field of Classification Search
None
See application file for complete search history.

(56) References Cited

U.S. PATENT DOCUMENTS

2005/0158719 A1  7/2005  Sato et al.
2008/0213759 A1  9/2008  Sato et al.
2008/0269129 A1  10/2008  Sato et al.
2010/0256224 A1  10/2010  Sato et al.
2011/0065641 A1  3/2011  Sato et al.

FOREIGN PATENT DOCUMENTS

| WO | WO 02/090546 A1 | 11/2002 |
| WO | WO 2006/073052 A1 | 7/2006 |
| WO | WO 2009/096425 A1 | 8/2009 |
| WO | WO 2010/024293 A1 | 3/2010 |

OTHER PUBLICATIONS

Shibuya et al Isolation and Characterization of Vasohibin-2 as a Homologue of VEGF-Inducible Endothelium-Derived Angiogenesis Inhibitor Vasohibin. Arterioscler Thromb Vasc Biol. 2006;26:1051-1057.*
International Search Report, issued Dec. 3, 2013, for International Application No. PCT/JP2013/080450.
Koyanagi et al., "Development of a Novel Molecular-targeted Therapy Against Vasohibin-2; Antitumor Effect of siRNA and Search for the Active Center of Vasohibin-2," The 20th Annual Meeting of the Japanese Vascular Biology and Medicine Organization, Dec. 5-7, 2012, 2 pages.
Koyanagi et al., "In Vivo Delivery of siRNA Targeting Vasohibin-2 Decreases Tumor Angiogenesis and Suppresses Tumor Growth in Ovarian Cancer," Cancer Science, 2013, pp. 1-6.
Sato "The Vasohibin Family: a Novel Family for Angiogenesis Regulation," J. Biochem, vol. 153, No. 1, 2013 (published online Oct. 25, 2012), pp. 5-11.
Shibuya et al, "Isolation and Characterization of Vasohibin-2 as a Homologue of VEGF-Inducible Endothelium-Derived Angiogenesis Inhibitor Vasohibin," Arterioscler Thromb Vasc Biol., vol. 26, published online Mar. 9, 2006, pp. 1051-1057.
Sun et al., "Generation and Characterization of Rabbit Polyclonal Antibodies Against Vasohibin-2 for Determination of its Intracellular Localization," International Journal of Oncology, vol. 43, 2013, pp. 255-261.
Takahashi et al., "Vasohibin-2 Expressed in Human Serous Ovarian Adenocarcinoma Accelerates Tumor Growth by Promoting Angiogenesis," Molecular Cancer Research, vol. 10, Sep. 2012, (published online Jul. 23, 2012), 8 pages.
Xue et al., "Vasohibin 2 is Transcriptionally Activated and Promotes Angiogenesis in Hepatocellular Carcinoma," Oncogene, vol. 32, 2013 (published online May 21, 2012), pp. 1724-1734.

* cited by examiner

*Primary Examiner* — Maher Haddad
(74) *Attorney, Agent, or Firm* — Birch, Stewart, Kolasch & Birch, LLP

(57) ABSTRACT

An anti-Vasohibin-2 antibody, a genetically recombinant anti-Vasohibin-2 antibody, or a fragment thereof, which recognizes amino acid numbers 269 to 288 of the amino acid sequence shown in SEQ ID NO: 2. The anti-Vasohibin-2 antibody of the present invention recognizes a Vasohibin-2 protein with an excellent specificity, and can inhibits an action of promoting angiogenesis owned by the Vasohibin-2 protein, so that the pharmaceutical composition containing the anti-Vasohibin-2 antibody is suitably used in the treatment of a disease requiring inhibition of angiogenesis such as cancer, and the like.

19 Claims, 8 Drawing Sheets

Mouse IgG (Negative Control)    VASH2 Antibody (Clone 1760)

×200, Bar=50μm

↑: Administration of Antibody
Day 0: At a point where tumor is measurable (about 1 week after tumor transplantation).

ANTI-VASOHIBIN 2 ANTIBODY

TECHNICAL FIELD

The present invention relates to an anti-Vasohibin-2 antibody. More specifically, the present invention relates to a monoclonal antibody or a fragment thereof specific to Vasohibin-2, a hybridoma producing the monoclonal antibody, a genetically recombinant antibody or a fragment thereof of the antibody, an angiogenesis inhibitor containing the above antibody or a fragment thereof, a pharmaceutical composition for treatment, a pharmaceutical composition for treatment of cancer, a method for assessing pharmacological efficacy of an anti-angiogenesis agent using the above antibody or a fragment thereof, and a kit for carrying out the method.

BACKGROUND ART

Angiogenesis refers to the phenomenon of formation of new blood vessels from pre-existing veinlets or capillary blood vessels in animal tissues or organs by migration, proliferation and lumen formation of vascular endothelial cells. The phenomenon is not only caused in the morphogenetic stages or growth stages of animals, but also caused along with the curing of damages of tissues, restoration processes of inflammations, and menstrual periods, which are controlled both by promoting factors and inhibiting factors of angiogenesis. Therefore, it is important to maintain a balance between the promoting factor and the inhibiting factor in order to maintain homeostasis of the blood vessels.

However, in tumor tissues, angiogenesis is enhanced by overexpression of the angiogenesis promoting factor, which consequently leads to a further augmentation of the tumor tissues. Therefore, as the anticancer therapy, a method of administering an angiogenesis inhibiting factor or an inhibitor for an angiogenesis promoting factor or the like has been considered.

Vasohibins are polypeptides found by the present inventors, to which Vasohibin-1 and Vasohibin-2 belong as homologues. These Vasohibins have been known to be expressed in the vascular endothelial cells by stimulations of angiogenesis promoting factors (VEGF, FGF-2 or the like) secreted from tumor cells, interstitial cells, macrophages, and the like, and act on the endothelial cells themselves in an manner, to have an action of inhibiting angiogenesis (see, Patent Publications 1 and 2).

On the other hand, the present inventors have also found that Vasohibin-2, i.e. AK022567 protein, and BC051856 protein, BC053836 protein, BC028194 protein, and AY834202 protein, which are splicing variants thereof, which are disclosed in Patent Publication 2, have actions of promoting angiogenesis in the same hypoxia state as pathologies such as cancer and cerebrovascular disorders, and reported (see, Patent Publication 3).

PRIOR ART REFERENCES

Patent Publications

Patent Publication 1: WO 2002/090546
Patent Publication 2: WO2006/073052
Patent Publication 3: WO2009/096425

SUMMARY OF THE INVENTION

Problems to be Solved by the Invention

An object of the present invention is to provide an antibody or a fragment thereof specific to Vasohibin-2 protein, a hybridoma produced by the antibody, a genetically recombinant antibody or a fragment thereof of the antibody, an angiogenesis inhibitor containing the above antibody or a fragment thereof and a pharmaceutical composition for treatment, and a method of assessing pharmacological efficacy of an anti-angiogenesis agent using the above antibody or a fragment thereof and a kit for carrying out the method.

Means to Solve the Problems

As a result of intensive studies, the present inventors have arrived at specifying an active center of the Vasohibin-2 protein. Moreover, as a result of preparing a monoclonal antibody against a specified epitope containing this active center of the Vasohibin-2 protein, the present inventors have found that the monoclonal antibody specifically binds to the Vasohibin-2 protein to inhibit angiogenesis action owned by the Vasohibin-2 protein. The present invention has been accomplished thereby.

In sum, the present invention relates to the following [1] to [10]:

[1] An anti-Vasohibin-2 antibody or a fragment thereof, which recognizes amino acid numbers 269 to 288 of the amino acid sequence shown in SEQ ID NO: 2.
[2] A genetically recombinant anti-Vasohibin-2 antibody or a fragment thereof, which recognizes amino acid numbers 269 to 288 of the amino acid sequence shown in SEQ ID NO: 2.
[3] A hybridoma that produces an anti-Vasohibin-2 monoclonal antibody recognizing amino acid numbers 269 to 288 of the amino acid sequence shown in SEQ ID NO: 2.
[4] An angiogenesis inhibitor containing the antibody or a fragment thereof as defined in the above [1] or [2].
[5] A pharmaceutical composition containing the antibody or a fragment thereof as defined in the above [1] or [2].
[6] A pharmaceutical composition for treatment of diseases requiring inhibition of angiogenesis, containing the angiogenesis inhibitor as defined in the above [4].
[7] A method for assessing pharmacological efficacy of an anti-angiogenesis agent, including:
step (A): contacting a biological sample derived from a test individual after administration of a candidate compound of the anti-angiogenesis agent, with the antibody or a fragment thereof as defined in the above [1] or [2], to form a complex, and measuring an existing amount of the complex;
step (B): comparing the existing amount measured in the above step (A) with an existing amount before administration; and
step (C): judging that it is highly possible that the candidate compound shows pharmacological efficacy as an anti-angiogenesis agent, in a case where the existing amount of the complex after administration of the candidate compound is smaller than that before administration, in the comparison carried out in the above step (B).
[8] A kit for assessing pharmacological efficacy of an anti-angiogenesis agent, containing the antibody or a fragment thereof as defined in the above [1] or [2].

[9] A method for treating diseases requiring inhibition of angiogenesis, including the step of administering the antibody or a fragment thereof as defined in the above [1] or [2] in a therapeutically effective amount to an individual in need of treating diseases requiring inhibition of angiogenesis.

[10] The antibody or a fragment thereof according to the above [1] or [2], for treating or preventing diseases requiring inhibition of angiogenesis.

Effects of the Invention

The anti-Vasohibin-2 antibody or a fragment thereof of the present invention exhibits some excellent effects capable of binding to Vasohibin-2 protein with favorable specificity, and inhibiting the angiogenesis promoting action thereof.

MODES FOR CARRYING OUT THE INVENTION

Figure 1:
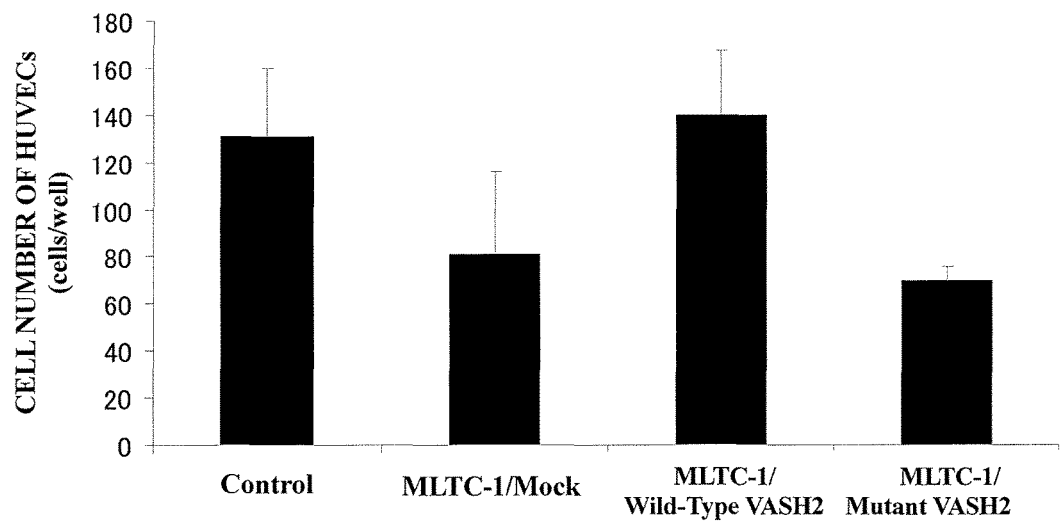
FIG. 1 is a graph showing effects of Vasohibin-2 on migration ability of endothelial cells.

The anti-Vasohibin-2 antibody of the present invention (hereinafter also referred to the antibody of the present invention) has the feature of binding specifically a Vasohibin-2 protein by recognizing a specified amino acid sequence.

Vasohibins include Vasohibin-1 and Vasohibin-2, and the Vasohibin in the present invention refers to Vasohibin-2. Here, as disclosed in Patent Publications 1, 2 and the like, Vasohibin-1 and Vasohibin-2 are separate genes existing on different chromosomes, and the amino acid sequences of proteins encoded by these genes have a 58% homology. Vasohibin-2 refers to a Vasohibin-2 protein encoded by AY834202 polynucleotide consisting of the nucleotide sequence shown in SEQ ID NO: 1, and AY834202 polypeptide consisting of the amino acid sequence shown in SEQ ID NO: 2.

As the epitope (determinant in an antigen) in the present invention, a partial peptide from the amino acid numbers 269 (Leu) to 288 (Arg) of the Vasohibin-2 protein, or a part thereof can be used. In the partial peptide, in a case where a Vasohibin-2 mutant is prepared by, for example, substituting five (5) contiguous amino acids from 281st (Lys) to 285th (Lys) with four (4) alanine (Ala) to be expressed in a cell, the promotion of angiogenesis was not found. Therefore, it is considered that the partial peptide containing the amino acids of the above amino acid numbers 281 to 285 is involved in exhibition of the action promoting angiogenesis. Therefore, in order to prepare an antibody for neutralizing action of promoting angiogenesis of the Vasohibin-2 protein, it is preferable that a partial peptide containing the amino acids of the above amino acid numbers 281 to 285 of the Vasohibin-2 protein is used as the epitope. Here, the antigen used in the preparation of the antibody is not limited within the range that the antibody of the present invention can be prepared, which may be a peptide containing any one of the epitopes in the present invention mentioned above. In other words, the antigen may be a partial peptide of the Vasohibin-2 protein that is longer than the epitope in the present invention, or a peptide bound to a peptide not associated with the Vasohibin-2 protein at a carboxyl terminal or amino terminal of the epitope in the present invention, and the antigen may be bound with a carrier protein such as KLH, OVA, or BSA, or Fc region of IgG.

The term "angiogenesis" as used herein means the phenomenon that vascular endothelial cells sprout from pre-existing blood vessels, and form capillary blood vessels in the manner of invading into the tissues. The formation process progresses in the order of 1) digestion of vascular basal membrane with protease, 2) migration and proliferation of vascular endothelial cells, and 3) lumen formation.

The antibody of the present invention may be those that recognize the amino acid numbers 269 to 288 of the amino acid sequence shown in SEQ ID NO: 2. In other words, the antibody may have bindability to an entire length of the partial peptide of the amino acid numbers 269 to 288, or may have bindability to a part of the amino acids, and it is preferable that the neutral antibody for neutralizing an action of promoting angiogenesis of the Vasohibin-2 protein has bindability to an epitope containing the amino acids of the amino acid numbers 281 to 285. Here, the antibody of the present invention may be a polyclonal antibody or a monoclonal antibody, within the range that recognizes the amino acid numbers 269 to 288 of the amino acid sequence shown in SEQ ID NO: 2, and a preferred embodiment includes a monoclonal antibody. The antibody of the present invention can be obtained by a method well known to one of ordinary skill in the art using an appropriate antigen described in the present specification. For example, the antibody includes a Vasohibin-2 monoclonal antibody or a fragment thereof produced by a hybridoma.

The monoclonal antibody using the hybridoma can be prepared by, for example, a method detailed hereinbelow.

First, an antigen is prepared. Concretely, a peptide in which a cysteine residue is added to the partial peptide Leu269-Arg288 of the Vasohibin-2 protein (hereinafter referred to as a Vasohibin-2 partial peptide) at an amino terminal or carboxyl terminal is synthesized in accordance with a known method. For the peptide obtained, a hapten antigen is prepared via an SH group of the peptide, using a maleimidated KLH [Keyhole Limpet Hemocyanin, Imject (registered trademark) Maleimide Activated mcKLH, manufactured by Pierce Biotechnology, Inc.].

Furthermore, a fusion protein of Fc region of rabbit IgG and a Vasohibin-2 partial peptide (Fc fusion Vasohibin-2 protein) can be also used as an antigen. This fusion protein can be prepared in accordance with a known method, and, for example, the Fc fusion Vasohibin-2 protein can be prepared by introducing a plasmid vector having an insertion of a polynucleotide sequence in which Fc is added to an amino terminal or carboxyl terminal of the Vasohibion-2 partial peptide into, for example, Freestyle 293-F Cells (Invitrogen) to transiently express a fusion protein, and thereafter purifying the fusion protein using a protein A column. Here, the expression and purification of the Fc fusion Vasohibin-2 protein can be carried out in accordance with known methods without particular limitations.

Next, a mammal is immunized using an antigen obtained as described above. The mammal is not particularly limited, and, in general, mice, rats, cows, rabbits, goats, sheep, guinea pigs and the like can be used. Among them, mice and rats are preferred, and mice are more preferred. The mice are exemplified by A/J type, BALB/C type, DBA/2 type, C57BL/6 type mice. In addition, the age of the mammal differs depending on the animal species to be used and not particularly limited, and, usually about 4 to about 12 weeks old, and preferably about 5 to about 10 weeks old, in cases of mice or rats. Here, these mammals can be selected taking into consideration compatibility with plasma cells to be subjected to cell fusion, for the production of the monoclonal antibody of the present invention.

The antigen is mixed with an adjuvant in order to enhance immune response and used as an immunogen. The adjuvant is not particularly limited, and a known adjuvant can be used. In addition, mixing of the adjuvant and the antigen can be carried out in accordance with a method known in the art in regard to the adjuvant to be used.

Immunization of a mammal is carried out in accordance with a method known in the art. For example, the immunization is carried out by administering an immunogen to a mammal with a subcutaneous, intradermal, intravenous and/or intraperitoneal injection. In addition, the administration of the immunogen may be repeatedly carried out several times after the first immunization, and dosing intervals thereof can be appropriately adjusted. Here, since immune response differs depending on the kinds and strains of the mammals to be immunized, the immunization schedule and the dose of the immunogen may be appropriately set in accordance with the animals to be used.

Thus, a desired antibody-producing cell can be prepared in the body of an immunized mammal. As the antibody-producing cell, a spleen cell excised after 3 to 5 days from a final administration of the immunogen is preferred. Here, in order to allow hypertrophy of the spleen of the immunized mammal, booster (additional injection of an immunogen) may be carried out. The amount of the immunogen to be administered by booster is desired to be about 4 to about 5 times the amount of the immunogen to be first administered, and can be appropriately increased or decreased with this amount as a measure.

Next, the obtained antibody-producing cell is subjected to cell fusion with a cell derived from myeloma (myeloma cell), to prepare a hybridoma.

Since the proliferative ability of a hybridoma depends on the kind of the myeloma cell usable in the cell fusion, the myeloma cell is preferably a cell which is excellent in proliferative ability. In addition, it is preferable that the myeloma cell is compatible with the mammal from which the antibody-producing cell to be fused is originated. As examples thereof, myeloma cells are exemplified by mouse myeloma P3U1, X63-Ag8.653 and the like.

As a method for cell fusion, a method known in the art can be used, which is exemplified by, for example, a method using polyethylene glycol (PEG), a method using Sendai virus, a method using an electrofusion device, and the like.

The obtained hybridoma can be separated by culturing the hybridoma in a selective medium in accordance with a known method. Here, in order to confirm whether or not a selected hybridoma produces the desired antibody, the conditioned medium is collected, and antibody titer assay can be carried out on the basis of a known method, for example, DELFIA method.

Thus, a hybridoma which produces a desired monoclonal antibody is obtained. The hybridoma can be subcultured in an ordinary medium, or can also be semi-permanently stored in a liquid nitrogen.

In order to obtain the desired monoclonal antibody from a hybridoma, the monoclonal antibody can be mass-produced by in vivo and in vitro culture methods. An in vitro culture method can be carried out by culturing a hybridoma in an appropriate serum medium or a serum-free medium, to produce a desired monoclonal antibody in the medium. According to this culture method, a desired antibody having relatively high purity can be obtained as a conditioned medium. In addition, an in vivo culture method can be carried out by injecting a hybridoma intraperitoneally to a mammal compatible with the hybridoma, for example, a mouse, and allowing the hybridoma to propagate, thereby capable of collecting a desired antibody in a large amount as mouse ascites.

The obtained conditioned medium and ascites of a mouse or the like can be used directly as a crude antibody solution. In addition, these crude antibody solutions can be purified in accordance with a conventional method, for example, by a proper combination of DEAE anion exchange chromatography, affinity chromatography, ammonium sulfate fractionation, PEG fractionation, ethanol fractionation or the like, to give a purified antibody.

Thus, the monoclonal antibody that recognizes the amino acid numbers 269 to 288 of the amino acid sequence shown in SEQ ID NO: 2 can be obtained.

In the present invention, a hybridoma which produces a specified monoclonal antibody may be prepared in accordance with the above method and used, and cells deposited at International Patent Organism Depositary, National Institute of Technology and Evaluation, Incorporated Administrative Agency (2-5-8 Kazusakamatari, Kisarazu-shi, Chiba-ken, Japan) under the accession number given hereinbelow can also be preferably used:

NITE BP-1474 (identification: 1760, date of receipt: Nov. 29, 2012)

The fragment of the above antibody may have an antigen binding fragment against the above epitope, i.e., a partial peptide from 269th (Leu) to 288th (Arg) amino acids of the Vasohibin-2 protein, or a part thereof. Here, it is preferable that the fragment for neutralizing an action of promoting angiogenesis of the Vasohibin-2 protein has an antigen binding fragment against an epitope containing amino acids 281 to 285 of the amino acid sequence. The form thereof is not particularly limited, and includes, for example, peptides including Fab, F(ab')2, Fab', scFv, diabody, dsFv, and CDR. These antibody fragments can be prepared in accordance with known techniques, and the antibody fragments can be prepared by, for example, proteolytic enzyme cleavages with enzymes such as papain (production of Fab fragments) and pepsin (production of F(ab')2 fragments).

In addition, one embodiment of the present invention also provides a genetically recombinant anti-Vasohibin-2 antibody or a fragment thereof of the antibody of the present invention.

The genetically recombinant antibody is not particularly limited, so long as the recombinant antibody recognizes the amino acid numbers 269 to 288 of the amino acid sequence shown in SEQ ID NO: 2, and the recombinant antibody may have a bindability against an entire length of the partial peptide of the amino acids 269 to 288 of the amino acid sequence, or may have bindability to a part of the peptide thereof. Here, as the neutralizing antibody for neutralizing an action of promoting angiogenesis of the Vasohibin-2 protein, an antibody having a bindability to an epitope containing amino acids 281 to 285 of the amino acid sequence is preferred. The genetically recombinant antibody is exemplified by, for example, humanized antibodies, human antibodies, and the like, in a case where a subject to be administered with the antibody is human, so that the antigenicity can be reduced in an individual to be administered with the antibody. The genetically recombinant antibody in the present invention can be obtained by altering a monoclonal antibody obtained by the above hybridoma or a fragment thereof by using a known genetically recombinant technique.

The humanized antibody includes human-type chimeric antibodies and human-type CDR (Complementarity Determining Region)-grafted antibodies. The human-type chimeric antibody can be prepared by expressing genes encoding heavy-chain variable regions (hereinafter referred to as VH) and light-chain variable regions (hereinafter referred to as VL) of the above monoclonal antibody, and genes encoding heavy-chain constant region (hereinafter referred to as CH) and light-chain constant region (hereinafter referred to as CL). The human-type CDR transplantation antibody can be prepared by transplanting an amino acid sequence of the CDR against VH and VL of the antibody of the present invention to VH and VL of a human antibody at an appropriate position.

The human antibody includes antibodies obtained from a human antibody phage library or human antibody-producing transgenic animal. Here, the human antibody phage library and the human antibody-producing transgenic animal can be prepared in accordance with known methods.

In addition, the fragment of the genetically recombinant antibody may be a fragment of the above genetically recombinant antibody, and the form and the preparation methods thereof are not particularly limited, so long as the fragment has an antigen-binding fragment against a partial peptide consisting of the amino acid numbers 269 to 288 of the amino acid sequence shown in SEQ ID NO: 2, or a part thereof, in the same manner as in the fragment of the antibody of the present invention. Here, it is preferable that the fragment for neutralizing an action of promoting angiogenesis of the Vasohibin-2 protein has an antigen-binding fragment against the epitope containing the amino acids 281 to 285 of the amino acid sequence.

The antibody or a fragment thereof may be modified with a sugar chain such as mannose, fucose, galactose, N-acetylglucosamine, and N-acetylneuraminic acid, within the range that would recognize the amino acid numbers 269 to 288 of the amino acid sequence shown in SEQ ID NO: 2.

Thus, the antibody or a fragment thereof of the present invention, and the genetically recombinant antibody or a fragment thereof of the antibody is obtained. Since these antibodies or fragments thereof specifically recognize the amino acid numbers 269 to 288 of the amino acid sequence of the AY834202 polypeptide, these antibodies or fragments thereof show excellent bindability to the Vasohibin-2 protein. Here, these antibodies or fragments may be also collectively referred to herein as the antibody or a fragment thereof of the present invention.

The present invention provides a pharmaceutical composition containing the antibody or a fragment thereof of the present invention. The present pharmaceutical composition includes an agent such as an angiogenesis inhibitor and a pharmaceutical composition for treatment as one of the embodiments.

The present invention also provides an angiogenesis inhibitor containing the antibody or a fragment thereof of the present invention.

The angiogenesis inhibitor of the present invention is substantially constituted by the antibody or a fragment thereof of the present invention, and the angiogenesis inhibitor exhibits some effects that the exhibition of the action of promoting angiogenesis owned by the Vasohibin-2 protein is inhibited by binding with the Vasohibin-2 protein at a site delivered via circulated blood.

The angiogenesis inhibitor of the present invention is not limited in the dosage form, so long as the angiogenesis inhibitor migrates in the circulated blood.

In addition, the present invention provides a pharmaceutical composition for treating a disease requiring inhibition of angiogenesis, containing the angiogenesis inhibitor of the present invention, in other words, a therapeutic agent.

The disease requiring inhibition of angiogenesis is not particularly limited, so long as the disease is observed with some therapeutic effects by inhibiting angiogenesis, and the disease includes, for example, vascular diseases, inflammatory diseases, entoptic neovascular diseases, reproductive system diseases, central nervous system diseases, cancer, and the like. Concrete examples include arteriosclerosis, hypertension, angina pectoris, arteriosclerosis obliterans, myocardial infarction, cerebral infarction, diabetic angiopathy, vascular malformation, hepatitis, pneumonitis, glomerular nephritis, thyroiditis, myelitis, synovitis, osteoclasia, chondrocladia, rheumatism, asthma, sarcoidosis, Crow-Fukase syndrome, pannus, allergic edema, ulcers, ascites, peritoneal sclerosis, tissue adhesion, diabetic retinopathy, retinal vein occlusion, aging macular degeneration, uterine dysfunction, placental dysfunction, ovarian hyperalgesia, follicular cyst, retinopathy, cerebral apoplexy, vascular dementia, Alzheimer disease, malignant neoplasms such as solid cancer such as ovarian cancer and colorectal cancer, angioma, hemangioenthelioma, sarcoma, Kaposi's sarcoma, and tumors of hematopoietic system.

The pharmaceutical composition for treatment of the present invention includes a pharmaceutical composition formulated by combining the angiogenesis inhibitor of the present invention with a known pharmaceutical carrier. Also, the pharmaceutical composition for treatment of the present invention can be blended with other component which can be used in the same application as the antibody or a fragment thereof of the present invention, for example, a known component having an action of inhibiting angiogenesis, besides the antibody or a fragment thereof of the present invention.

The production of the pharmaceutical composition for treatment of the present invention can be usually carried out by blending an angiogenesis inhibitor of the present invention with a liquid or solid carrier that is pharmaceutically acceptable, so long as the pharmaceutical composition can be produced into a dosage form that the antibody or a fragment thereof of the present invention can reach to a site requiring inhibition of angiogenesis via circulated blood, and a solvent, a dispersant, an emulsifying agent, a buffer, a stabilizer, an excipient, a binder, a disintegrant, a lubricant or the like may be added as desired, so that a solid preparation such as tablet, granule, powder, fine powder, or capsule, or a liquid preparation such as liquid, suspension, or emulsion can be formed. In addition, a dry product which can be liquefied by addition of a suitable carrier before use, or an external agent can be formed. Here, the pharmaceutical carrier can be selected depending upon the dosing forms and formulation forms of the therapeutic agent, without being particularly limited thereto. The site requiring inhibition of angiogenesis as used herein means a site of the incidence of the above disease requiring inhibition of angiogenesis.

The pharmaceutical compositions for treatment in various formulation forms mentioned above can be appropriately produced by a conventional method utilizing a known pharmaceutical carrier or the like. In addition, the content of the antibody or a fragment thereof of the present invention in the pharmaceutical composition for treatment is not particularly limited, so long as the content is an amount that can obtain the exhibition of the desired effects of the present invention by taking into consideration the dosing forms, the administration methods, and the like. The content of the antibody or a fragment thereof of the present invention is usually from 1 to 100% by weight or so, of the pharmaceutical composition for treatment of the present invention. Here, the content of the antibody or a fragment thereof of the present invention as used herein means a total content in a case where the antibody and a fragment thereof of the present invention are contained in plural kinds.

The pharmaceutical composition for treatment of the present invention is administered by an appropriate administration method in accordance with the formulation form. The administration method is also not particularly limited, so long as the antibody or a fragment thereof of the present invention can be delivered via circulated blood, which can be administered internally, externally, and with an injection. In a case where the pharmaceutical composition for treatment of the present invention is administered with an injection, the pharmaceutical composition can be administered intravenously, intramuscularly, subcutaneously or intradermally. When administered by external application, the pharmaceutical composition may be administered by a suitable administration method as an external agent such as a suppository.

The dose of the pharmaceutical composition for treatment of the present invention is appropriately set and not a certain level, depending upon the formulation form, the administration method, the purpose of use, and age, body weight, and symptoms of a suffering individual (patient) or a suffering animal to which the pharmaceutical composition is administered. In addition, the administration may be performed in a single dose, or several divided doses in one day, within the desired dose range. Also, the administration period is optional.

The present invention also provides a method for treating a disease requiring inhibition of angiogenesis, including administering the antibody or a fragment thereof of the present invention in an effective amount to a test individual.

The test individual as used herein is preferably human requiring inhibition of angiogenesis, and the test individual may be a mammal in which angiogenesis is promoted with the Vasohibin-2 protein, which may be a livestock animal such as cow, horse, or goat; a pet animal such as dog, cat, or rabbit; or an experimental animal such as mouse, rat, guinea pig, or monkey.

Also, the effective amount as used herein is an amount of an antibody or a fragment thereof of the present invention that inhibits angiogenesis, as compared to a test individual not being dosed, in a case where the antibody or a fragment thereof is administered to a test individual mentioned above. A concrete effective amount is appropriately set and not a certain level, depending upon the dosage form, the administration method, the purpose of use, and age, body weight, and symptoms of a test individual.

In the method for treating a disease requiring inhibition of angiogenesis of the present invention, the antibody or a fragment thereof of the present invention may be directly administered to the above test individual in an effective amount, or may be administered as a medicament such as a pharmaceutical composition for treatment as mentioned above. Also, the administration method is not particularly limited, and for example, the antibody or a fragment thereof may be administered orally or with an injection or the like, in the same manner as in the above pharmaceutical composition for treatment.

According to the method of treatment of the present invention, some effects are exhibited that a disease to be administered with the above pharmaceutical composition for treatment of the present invention can be treated, and, for example, a disease that is developed by angiogenesis is treated.

The present invention provides a diagnostic agent, containing the antibody or a fragment thereof of the present invention. By using the present diagnostic agent, a disease to be administered with the above pharmaceutical composition for treatment of the present invention can be diagnosed.

The present inventors have reported that the Vasohibin-2 protein is expressed in cancer cells (see, Xue et al. *Oncogene*. 2012 [Epub ahead of print], Takahashi et al. *Mol. Cancer Res.* 10 (2012), 1135-1146.). Therefore, by using the diagnostic agent of the present invention, the Vasohibin-2 protein can be detected in a live body sample collected from a test individual, for example, blood, plasma, tissues, or the like, so that whether or not the test individual suffers from a disease developed by angiogenesis with the Vasohibin-2 protein, such as cancer, can be diagnosed, on the basis of the presence or absence of the detected Vasohibin-2 protein, or the amount of the Vasohibin-2 protein. For example, an amount of the Vasohibin-2 protein that is detected with the diagnostic agent according to the present invention in a live body sample collected from a test individual is compared with an amount of the Vasohibin-2 protein that is detected with the diagnostic agent according to the present invention in a live body sample collected from a control normal individual, and when the amount of Vasohibin-2 protein is significantly larger in a test individual than a control normal individual, the test individual can be diagnosed to be suffering from a disease developed by angiogenesis. Here, in the diagnostic method using the present diagnostic agent, as the detection method and the quantifying method of the Vasohibin-2 protein, methods well-known to one of ordinary skill in the art can be employed.

In addition, one embodiment of the present invention provides a method for assessing pharmacological efficacy of an anti-angiogenesis agent.

The present inventors have reported that Vasohibin-2 protein is secreted from cancer cells, and tumor angiogenesis and tumor proliferation are inhibited by knock-down of vasohibin-2 (see, Xue et al. *Oncogene.* 2012 [Epub ahead of print], Takahashi et al. *Mol. Cancer Res.* 10 (2012), 1135-1146.). Therefore, it is considered in an individual administered with an anti-angiogenesis agent that angiogenesis in tumor tissues is inhibited, and proliferation of tumor tissues is inhibited, so that the amount of the Vasohibin-2 secreted is reduced, and the blood level of Vasohibin-2 would possibly vary. Although the reactivity of the anti-angiogenesis agent against cancer cells in each individual is predicted to be different among individuals, the reactivity directly reflects an anti-angiogenesis effect owned by these agents. Therefore, in the method for assessing pharmacological efficacy of the present invention, it is considered that it is possible to predict the reactivity to the agent in each individual, or to assess the pharmacological efficacy after the actual administration by measuring a fluctuated amount of the blood level of the Vasohibin-2 protein before and after the administration of these agents.

The above method for assessing pharmacological efficacy concretely includes:
step (A): contacting a biological sample derived from a test individual after administration of a candidate compound of the anti-angiogenesis agent, with the antibody or a fragment thereof of the present invention, to form a complex, and measuring an existing amount of the complex;
step (B): comparing the existing amount measured in the above step (A) with an existing amount before administration; and
step (C): judging that it is highly possible that the candidate compound shows pharmacological efficacy as an anti-angiogenesis agent, in a case where the existing amount of the complex after administration of the candidate compound is smaller than that before administration, in the comparison carried out in the above step (B).

In the measurement of the existing amount of the complex in the step (A) of the above method for assessing pharmacological efficacy, a method well-known to one of ordinary skill in the art can be employed, so long as the method uses the antibody or a fragment thereof of the present invention, and a sandwich ELISA method is preferred. Here, the complex as referred to herein means a complex formed between the antibody or a fragment thereof of the present invention and the Vasohibin-2 protein. In addition, a test individual may be exemplified to be the same as above, and especially when the pharmacological efficacy of a novel anti-angiogenesis candidate substance is assessed and an effective substance is selected, it is preferable that an experimental animal other than human is a test individual. On the other hand, according to the present method for assessing pharmacological efficacy, in a case where whether or not the anti-angiogenesis agent is effective in the individual, it is preferable that human is a test individual.

In the step (B), the existing amount obtained above is compared by performing statistical analysis based on the existing amount before administration of the candidate compound. The analysis method is not particularly limited, and a known method can be used. In addition, the judgment in the subsequent step (C) is made such that it is highly possible that the candidate compound shows an effect of inhibiting angiogenesis as an anti-angiogenesis agent, in a case where the existing amount of the complex in the sample after administration of the candidate compound is smaller than that before administration.

Another embodiment of the present invention is to provide a kit for assessing pharmacological efficacy of an anti-angiogenesis agent.

The kit of the present invention includes a kit containing the antibody or a fragment thereof of the present invention, and the above kit can be used so long as the detection method is carried out using the antibody or a fragment thereof of the present invention when the Vasohibin-2 protein is detected in the sample. Since it is possible that the antibody or a fragment thereof of the present invention recognizes a Vasohibin-2 protein in a live body with an excellent specificity, the use of the kit brings on great contributions in the assessment of the pharmacological efficacy of the anti-angiogenesis agents.

EXAMPLES

The present invention will be described more specifically by showing Examples and Comparative Examples, without intending to limit the present invention to the following Examples.

Reference Example 1

Effects of Vasohibin-2 on Migration Ability of Endothelial Cells

Each of Mock gene, a gene encoding AY834202 polypeptide as a wild-type Vasohibin-2 (wild-type VASH2), a gene encoding a polypeptide obtained by substituting five (5) amino acids of the amino acid numbers 281 to 285 of the AY834202 polypeptide with four (4) alanine as a mutant Vasohibin-2 (mutant VASH2) was introduced to MLTC-1 cells, and the cells obtained (MLTC-1/Mock, MLTC-1/wild-type VASH2, MLTC-1/mutant VASH2) were spread on a 24-well plate in an amount of $1 \times 10^5$ cells/well. The cells were cultured in a medium containing 0.5% sera for 24 hours. Thereafter, $5 \times 10^4$ human umbilical vein endothelial cells (HUVECs) previously cultured in a low-serum medium for 17 hours were added to a culture insert having a pore size of 8 µm, and the cells were incubated at 37° C. for 4 hours, and the HUVECs migrated to a lower side of the membrane were stained with Giemsa. The HUVECs migrated to a lower side were randomly counted in 5 fields at a magnification of 200 under an optical microscope, and a mean and standard deviations were calculated. The results are shown in FIG. 1. Here, the migration ability test of the endothelial cells is one of the representative assay methods for in vitro angiogenesis.

The conditioned medium of MLTC-1/wild-type VASH2 significantly promoted the migration of HUVECs as compared to that with Mock ($p<0.01$); however, the migration promoting effects were not observed in the conditioned medium of MLTC-1/mutant VASH2, as compared to that with Mock.

Reference Example 2

Effects of Vasohibin-2 on Network Formation of Endothelial Cells

Figure 2:
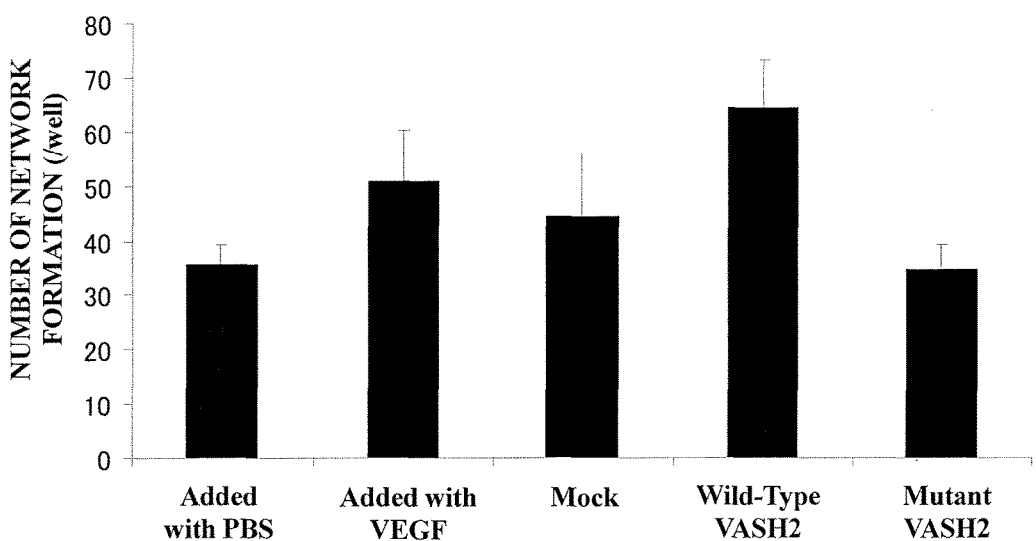
FIG. 2 is a graph showing effects of Vasohibin-2 on tube formation of endothelial cells.

A 500 μL growth factor-free Matrigel (BD Biosciences) was added to each of the wells of a 24-well plate to allow gelation, and 7.5×10$^4$ HUVECs previously cultured in a low-serum medium for 17 hours (suspended in 500 μL) were spread thereon. A 500 μL conditioned medium of each of MLTC-1/Mock, MLTC-1/wild-type VASH2, and MLTC-1/mutant VASH2 obtained in Reference Example 1 was added thereto, and the cells were incubated at 37° C. for 5 hours. The branching point of the formed network was counted in five (5) fields randomly at a magnification of 40 under a phase-contrast microscope, and a mean and standard deviations were calculated. The group added with PBS was used as a negative control, and the group added with VEGF 20 ng/mL was used as a positive control. The results are shown in FIG. 2. Here, the network forming ability examination of the endothelial cells is one of the representative assay methods for in vitro angiogenesis.

When the conditioned medium of MLTC-1/wild-type VASH2 was added, the network formation by the HUVECs was significantly promoted as compared to that with Mock ($p<0.01$); however, when the conditioned medium of MLTC-1/mutant VASH2 was added, the network formation promoting effects were not observed.

It was clarified from these findings that the amino acids of the amino acid numbers 281 to 285 of the AY834202 polypeptide are associated with the activity of promoting the migration of HUVECs.

Preparation Example 1

Preparation of Monoclonal Antibody (Preparation of Antigen)

As a Vasohibin-2 protein, a peptide obtained by adding a cysteine residue to an amino terminal or carboxyl terminal of the amino acid numbers 281 to 285 of the AY834202 polypeptide was synthesized by Sigma-Aldrich, and each of these resultant peptides was named clones 71, 1694, 1760, and 2356, respectively. For each of the peptides obtained, a hapten antigen was prepared via an SH group of the peptide using Maleimide Activated KLHs [Keyhole Limpet Hemocyanin, Imject (registered trademark) Maleimide Activated mcKLH, manufactured by Pierce]. Here, the AY834202 polypeptide was prepared in accordance with the method described in Patent Publication 3.

(Preparation of Monoclonal Antibody)

The hapten antigen of Vasohibin-2 was mixed in an equal volume with a complete adjuvant for a first immunization, or with an incomplete adjuvant for second and subsequent immunizations, to prepare an emulsion as an immunogen.

The monoclonal antibody was prepared as follows. 5-week old female Balb/c line mice were intraperitoneally administered with a mixture of 50 μg of a hapten antigen with an adjuvant such as FCA per mouse, per administration. With intervals of 2 weeks or longer, immunization was repeated, and as a final booster 50 μg of a hapten antigen was administered to mice with elevated antibody titer against the antigen peptide from tail vein. After 3 days from the final boost, the spleen was excised from the mice, to prepare splenocytes. The cell fusion of the splenocytes and the myeloma cells (p3.x63.Ag8.653) was carried out using PEG method, to prepare a hybridoma.

Each of the monoclonal antibodies was purified using the protein A column (MAPS II kit, Bio-Rad Laboratories Inc.) from ascites obtained by administering to mice a serum-free medium of an antibody-producing hybridoma or a hybridoma.

Example 1

Effects of Monoclonal Antibody on Migration Ability of Endothelial Cells

MLTC-1/wild-type VASH2 cells were spread on a 24-well plate in an amount of 1×10$^5$/well, and cultured in a medium containing 0.5% sera for 24 hours, and thereafter 5×10$^4$ HUVECs previously cultured in a low-serum medium for 17 hours were added to a culture insert having a pore size of 8 μm. Thereafter, each of clones 71, 1694, 1760, and 2356 of mouse IgG, mouse anti-sera (polyclonal antibody), and anti-human VASH2 monoclonal antibody was added to a lower chamber at a concentration of 5 μg/mL. The cells were incubated at 37° C. for 4 hours, and the HUVECs migrated to a lower side of the membrane were stained with Giemsa. The HUVECs migrated to a lower side were randomly counted in 5 fields at a magnification of 200 under an optical microscope, and a mean and standard deviations were calculated. The group spread with MLTC-1/Mock was used as a negative control. The results are shown in FIG. 3.

Figure 3:
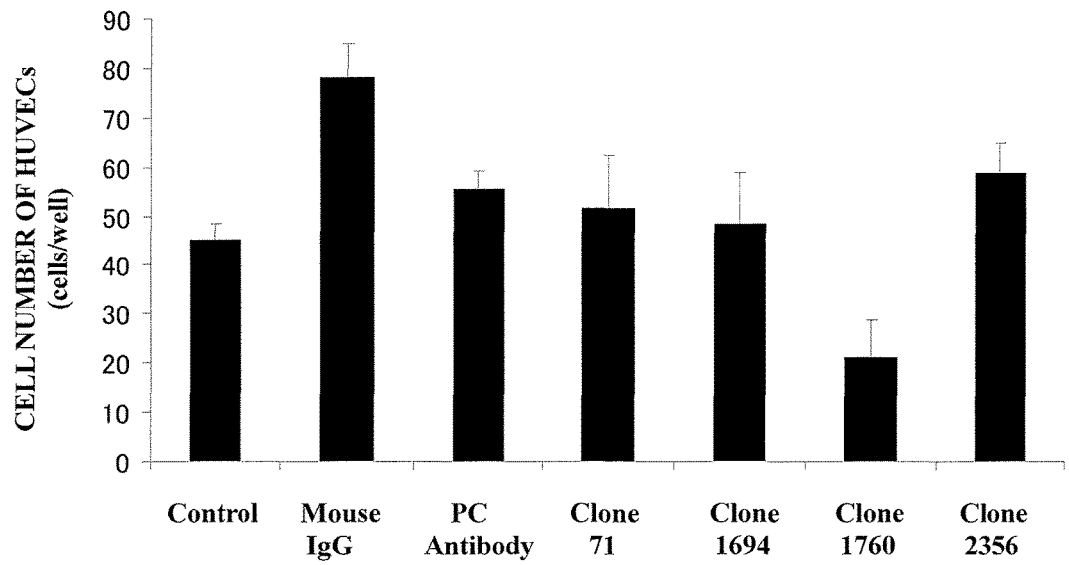
FIG. 3 is a graph showing effects of monoclonal antibodies on migration ability of endothelial cells.

From FIG. 3, all of the groups added with the polyclonal antibody or each of the monoclonal antibody had significant inhibition of the migration of endothelial cells, as compared to the group added with mouse IgG, and clone 1760 had the greatest inhibiting effect ($p<0.01$).

Example 2

Effects of Monoclonal Antibody on Network Formation of Endothelial Cells

A 500 μL growth factor-free Matrigel (BD Biosciences) was added to each of the wells of a 24-well plate to allow gelation, and 7.5×10$^4$ HUVECs previously cultured in a low-serum medium for 17 hours (suspended in 500 μL) were spread thereon, and a 500 μL conditioned medium of MLTC-1/wild-type VASH2 was added thereto. At this time, each of mouse IgG, mouse antisera (polyclonal antibody), clones 71 and 1760 of anti-human VASH2 monoclonal antibody, or a monoclonal antibody 5E3 previously prepared by using a partial peptide of the amino acid numbers 207 (serine) to 219 (lysine) of the AY834202 polypeptide as an antigen was added to a lower chamber at a concentration of 5 μg/mL. The cells were incubated at 37° C. for 5 hours. The branching point of the formed network was counted in five (5) fields randomly at a magnification of 40 under a phase-contrast microscope, and a mean and standard deviations were calculated. The group spread with MLTC-1/Mock was used as a negative control. The results are shown in FIG. 4.

Figure 4:
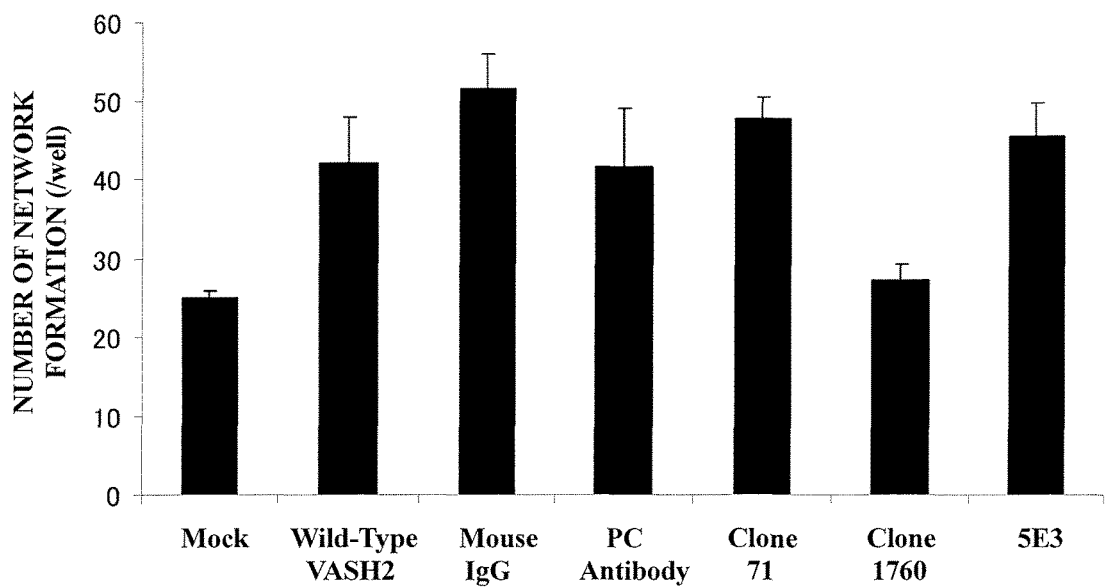
FIG. 4 is a graph showing effects of monoclonal antibodies on tube formation of endothelial cells.

From FIG. 4, all of the groups added with clones 71 and 1760, and 5E3 had significant inhibition of the network formation, as compared to the group added with mouse IgG, and the group added with clone 1760 had the greatest inhibiting effect ($p<0.01$), in the same manner as the migration experiment. The anti-VASH2 monoclonal (5E3) previously prepared that recognizes a different amino acid sequence was not found to have neutralizing activity.

It was clarified from the above results that the prepared monoclonal antibodies have neutralizing activity against the Vasohibin-2 protein, among which clone 1760 had the highest neutralizing activity.

Example 3

Mouse Tumor Model-1

A suspension of $1 \times 10^6$ human ovarian serous adenocarcinoma cell line (SKOV-3) in 100 μL of PBS was transplanted subcutaneously to the back part of 6- to 8-week old, female BALB-c nude mice (n=4). At a time point when a tumor was measurable (diameter of 5 mm or so), mouse IgG (5 mg/kg) or clone 1760 of an anti-human VASH2 monoclonal antibody (5 mg/kg) was intraperitoneally administered. In addition, the tumor diameter was measured at the time of administering the antibody, and a tumor volume was calculated by the formula of length×width×width×½, and an average was calculated. The antibodies were administered for a total of 6 times (day 0, day 4, day 7, day 12, day 15, and day 19), and the tumor was excised on day 22 from the beginning of the treatment. The representative photograph of the tumor immediately before excision is shown in FIG. 5, and changes in tumor volumes are shown in FIG. 6.

Figure 5:
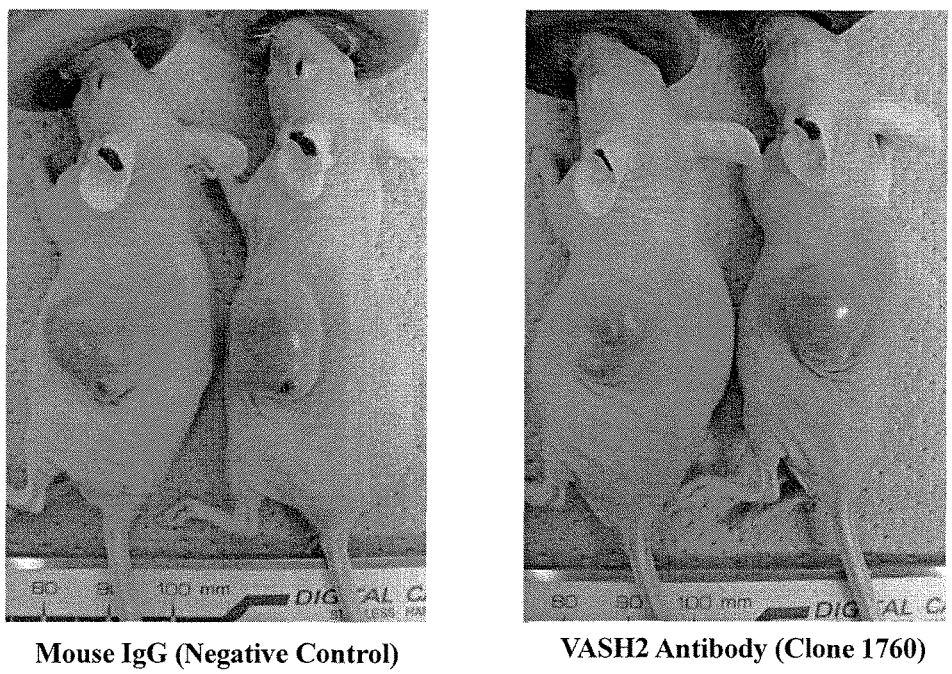
FIG. 5 is some views showing tumor morphologies in mice tumor models after administration of the monoclonal antibody, wherein the left panel is the group administered with mouse IgG, and the right panel is the group administered with an anti-VASH2 antibody (clone 1760).
Figure 6:
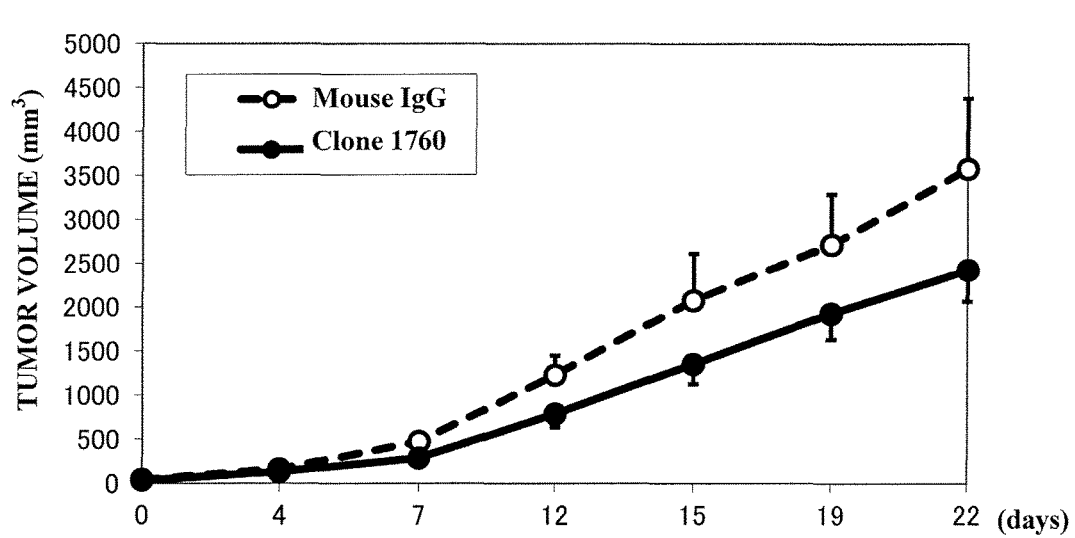
FIG. 6 is a graph showing tumor volume changes in mice tumor models after administration of the monoclonal antibody.

From FIGS. 5 and 6, the group administered with clone 1760 had significant inhibition of tumor proliferation as compared to the group administered with mouse IgG (p<0.05), and showed a 33% reduction in the tumor volume.

In addition, the blood vessels of the excised tumor were visualized by immunostaining, and the proportion of the vascular cross-sectional areas in the tumor area was calculated. The representative photograph of the tumor blood vessel is shown in FIG. 7, and the comparison of the cross-sectional areas is shown in FIG. 8.

Figure 7:
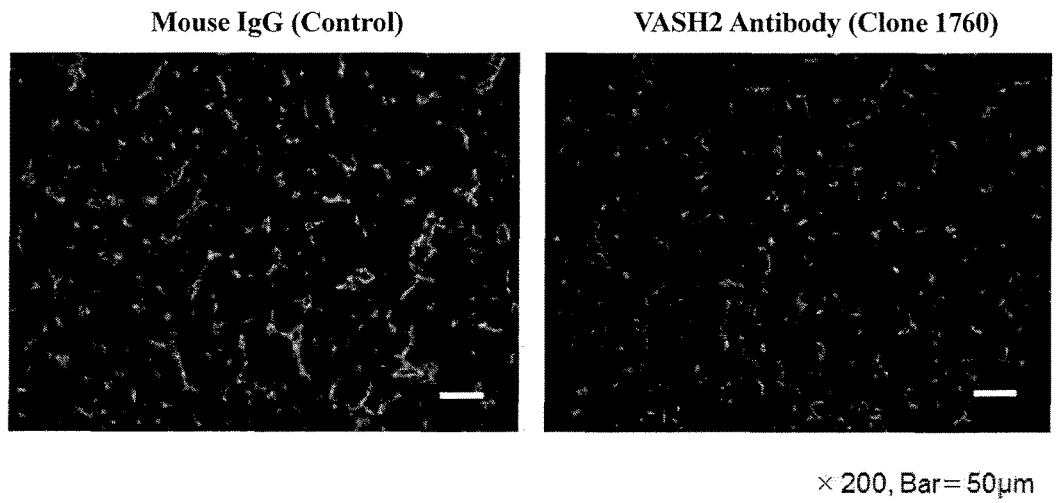
FIG. 7 is some views showing tumor blood vessels in mice tumor models after administration of the monoclonal antibody, wherein the left panel is the group administered with mouse IgG, and the right panel is the group administered with an anti-VASH2 antibody (clone 1760).
Figure 8:
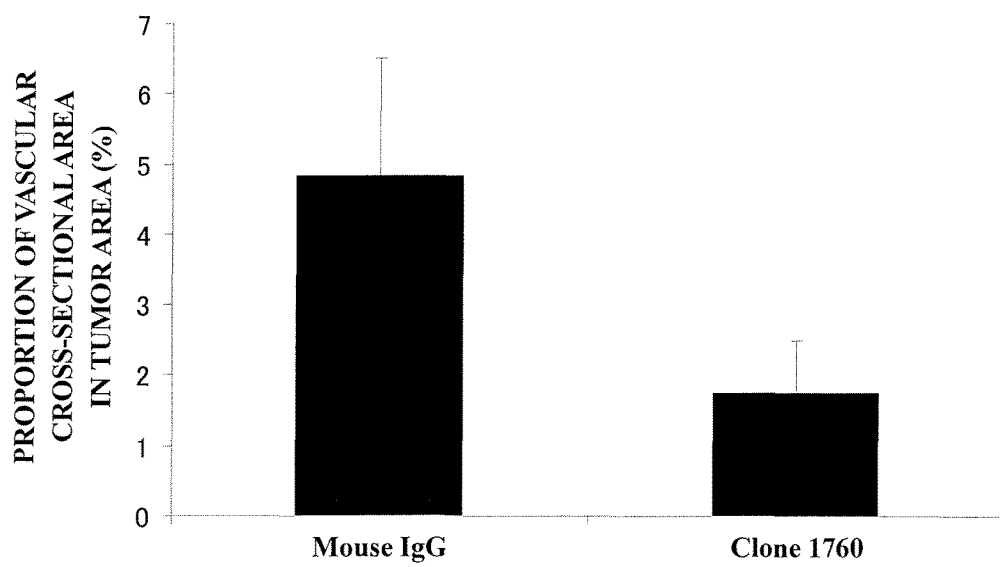
FIG. 8 is a graph quantitatively showing vascular cross-sectional area changes of tumors in mice tumor models after administration of the monoclonal antibody.

From FIGS. 7 and 8, the group administered with clone 1760 was found to have a significant reduction in the vascular cross-sectional area of the tumor, as compared to the group administered with mouse IgG (p<0.01), and the effect of inhibiting tumor angiogenesis was confirmed on an individual level.

Example 4

Mouse Tumor Model-2

$1 \times 10^6$ human ovarian serous adenocarcinoma cell line (SKOV-3) was transplanted subcutaneously to the back part of 6- to 8-week old, female BALB-c nude mice (n=8), in the same manner as in Example 3. At a time point when a tumor was measurable (diameter of 5 mm or so, about a week later), mouse IgG (5 mg/kg), clone 1760 of an anti-human VASH2 monoclonal antibody (10, 15, 25, or 50 mg/kg), or an angiogenesis inhibitor bevacizumab (manufactured by CHUGAI PHARMACEUTICAL CO., LTD., 5 mg/kg) was intraperitoneally administered. In addition, the tumor diameter was measured at the time of administering the antibody, and a tumor volume was calculated by the formula of length×width×width×½, and an average was calculated. The antibodies were administered for a total of 5 times (day 0, day 4, day 7, day 11, and day 14), and the tumor was excised on day 18 from the beginning of the treatment. The tumor volume on day 18 is shown in FIG. 9.

Figure 9:
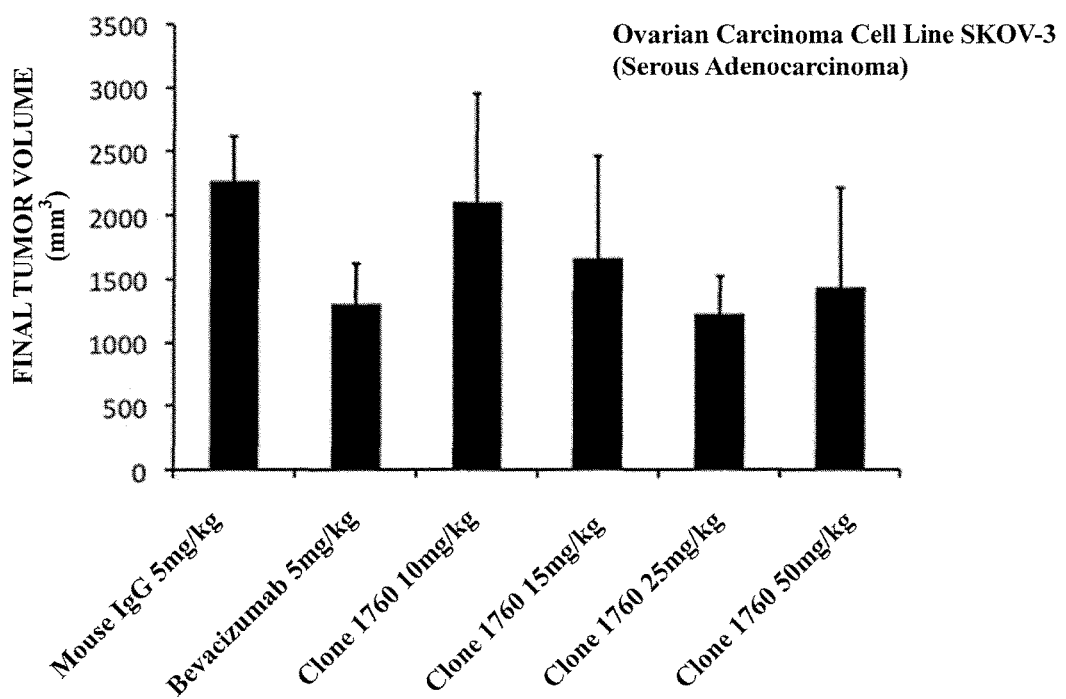
FIG. 9 is a graph showing mouse tumor volumes after administration of mouse IgG, bevacizumab, or the monoclonal antibody.

It can be seen from FIG. 9 that the group administered with bevacizumab (5 mg/kg) and the group administered with clone 1760 (25 mg/kg) show nearly the same level of the effects of inhibiting tumor proliferation.

Figure 10:
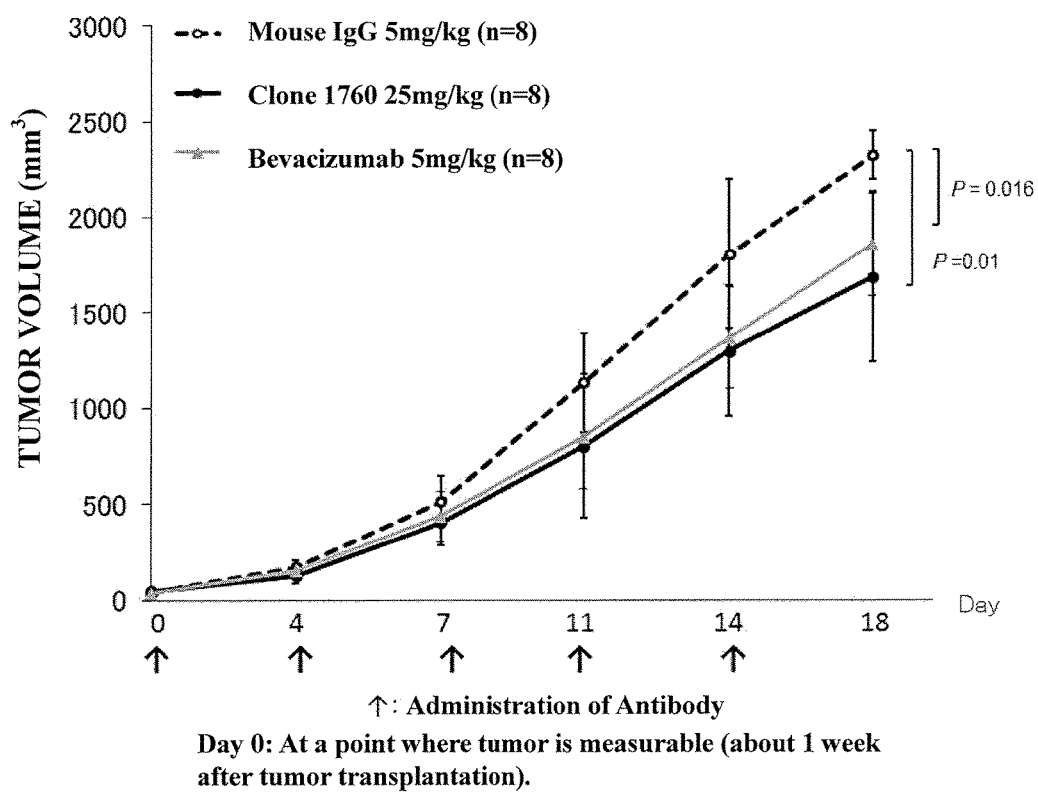
FIG. 10 is a graph showing mouse tumor volume changes in mice tumor models after administration of mouse IgG, bevacizumab, or the monoclonal antibody.

Also, changes in tumor volumes in the group administered with mouse IgG (5 mg/kg), the group administered with clone 1760 (25 mg/kg), and the group administered with bevacizumab (5 mg/kg) are shown in FIG. 10.

It can be seen from FIG. 10 that the group administered with bevacizumab inhibits tumor proliferation at p<0.016, as compared to the group administered with mouse IgG, whereas the group administered with clone 1760 inhibits the tumor proliferation at p<0.010, and that the progress of the inhibiting effects is also nearly the same.

Further, the blood vessels of the excised tumor were visualized by immunostaining, and the proportion of the vascular cross-sectional areas in the tumor area was calculated. The representative photographs of the group administered with mouse IgG (5 mg/kg), the group administered with clone 1760 (25 mg/kg), and the group administered with bevacizumab (5 mg/kg) are shown in FIG. 11, and the comparison of the cross-sectional areas is shown in FIG. 12.

Figure 11:
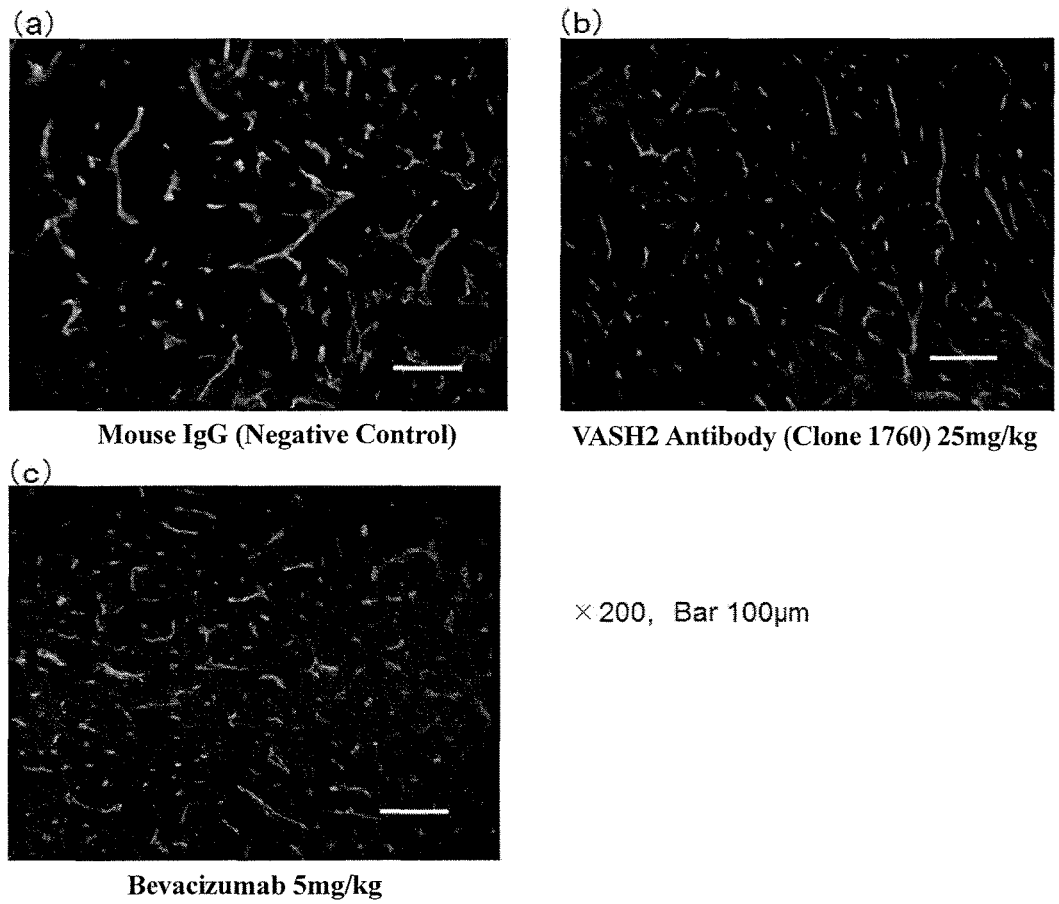
FIG. 11 is some views showing tumor blood vessels in mice tumor models after administration of the monoclonal antibody, wherein panel (a) is the group administered with mouse IgG, panel (b) is the group administered with an anti-VASH2 antibody (clone 1760), and panel (c) is the group administered with bevacizumab.
Figure 12:
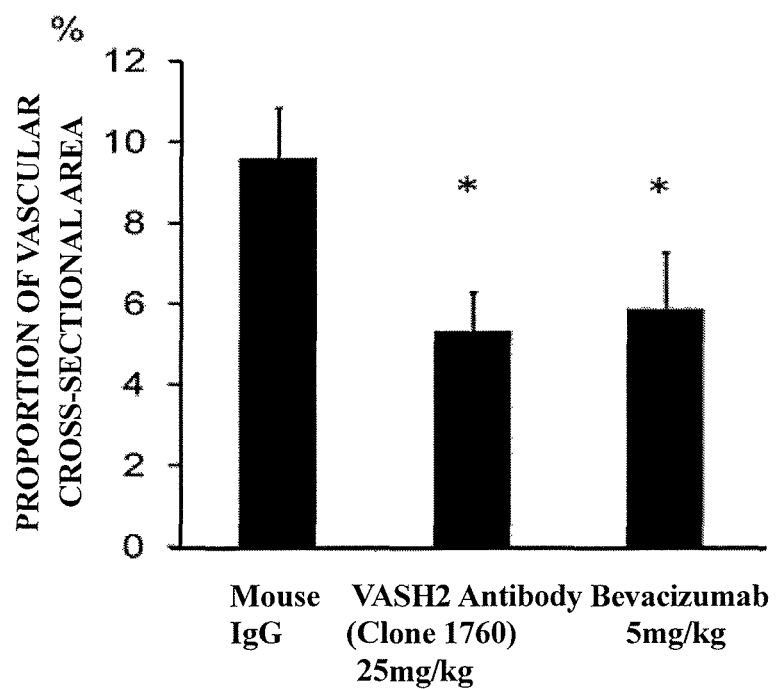
FIG. 12 is a graph quantitatively showing proportions of vascular cross-sectional areas of tumors in mice tumor models after administration of mouse IgG, bevacizumab, or the monoclonal antibody.

From FIGS. 11 and 12, the group administered with clone 1760 was found to have a significant reduction in the vascular cross-sectional areas of the tumor, as compared to the group administered with mouse IgG (p<0.01), so that the effect of inhibiting tumor angiogenesis was confirmed on an individual level.

The present inventors have elucidated that Vasohibin-2 is expressed in liver cancer or ovarian cancer of human, and the tumor angiogenesis or the tumor growth can be inhibited by knock-down of the expression of the Vasohibin-2. Also, the present inventors have previously established a monoclonal antibody 5E3 recognizing the amino acid numbers 207 to 219 of the AY834202 polypeptide, but an anti-Vasohibin-2 antibody reported to have neutralizing activity was not found. Therefore, in the present invention, it was clarified for the first time that the anti-Vasohibin-2 antibody of the present invention can inhibit the tumor growth. In view of the above, the antibody of the present invention has been expected for cancer treatment or applications to ophthalmic diseases, with the purpose of controlling the abnormal angiogenesis.

INDUSTRIAL APPLICABILITY

The anti-Vasohibin-2 antibody of the present invention recognizes a Vasohibin-2 protein with an excellent specificity, and can inhibits an action of promoting angiogenesis owned by the Vasohibin-2 protein, so that the pharmaceutical composition containing the anti-Vasohibin-2 antibody is suitably used in the treatment of a disease requiring inhibition of angiogenesis such as cancer, and the like.

SEQUENCE FREE TEXT

SEQ ID NO: 1 of the Sequence Listing is AY834202 polynucleotide.

SEQ ID NO: 2 of the Sequence Listing is AY834202 polypeptide.

The invention claimed is:

1. An anti-Vasohibin-2 antibody or a fragment thereof, which recognizes amino acid numbers 269 to 288 of the amino acid sequence shown in SEQ ID NO: 2.

2. The antibody or a fragment thereof according to claim 1, which is a monoclonal antibody.

3. The antibody or a fragment thereof according to claim 2, produced by a hybridoma shown by the accession number NITE BP-1474.

4. A genetically recombinant anti-Vasohibin-2 antibody or a fragment thereof, which recognizes amino acid numbers 269 to 288 of the amino acid sequence shown in SEQ ID NO: 2.

5. A hybridoma that produces an anti-Vasohibin-2 monoclonal antibody recognizing amino acid numbers 269 to 288 of the amino acid sequence shown in SEQ ID NO: 2.

6. The hybridoma according to claim 5, which is shown by the accession number NITE BP-1474.

7. An angiogenesis inhibitor comprising the antibody or a fragment thereof as defined in claim 1.

8. A pharmaceutical composition comprising the antibody or a fragment thereof as defined in claim 1.

9. A pharmaceutical composition for treatment of tumor angiogenesis, comprising the angiogenesis inhibitor as defined in claim 7.

10. A method for assessing pharmacological efficacy of an anti-angiogenesis agent, comprising:

step (A): contacting a biological sample derived from a test individual after administration of a candidate compound of the anti-angiogenesis agent, with the antibody or a fragment thereof as defined in claim 1, to form a complex, and measuring an existing amount of the complex;

step (B): comparing the existing amount measured in the above step (A) with an existing amount before administration; and step (C): judging that it is highly possible that the candidate compound shows pharmacological efficacy as an anti-angiogenesis agent, in a case where the existing amount of the complex after administration of the candidate compound is smaller than that before administration, in the comparison carried out in the above step (B).

11. A kit for assessing pharmacological efficacy of an anti-angiogenesis agent, comprising the antibody or a fragment thereof as defined in claim 1.

12. A method for treating tumor angiogenesis, comprising the step of administering the antibody or a fragment thereof as defined in claim 1 in a therapeutically effective amount to an individual in need of treating the tumor angiogenesis.

13. The antibody or a fragment thereof according to claim 1, for treating tumor angiogenesis.

14. An angiogenesis inhibitor comprising the antibody or a fragment thereof as defined in claim 2.

15. An angiogenesis inhibitor comprising the antibody or a fragment thereof as defined in claim 3.

16. An angiogenesis inhibitor comprising the antibody or a fragment thereof as defined in claim 4.

17. A pharmaceutical composition comprising the antibody or a fragment thereof as defined in claim 2.

18. A pharmaceutical composition comprising the antibody or a fragment thereof as defined in claim 3.

19. A pharmaceutical composition comprising the antibody or a fragment thereof as defined in claim 4.

* * * * *

SEQUENCE LISTING

<160> NUMBER OF SEQ ID NOS: 2

<210> SEQ ID NO 1
<211> LENGTH: 1068
<212> TYPE: DNA
<213> ORGANISM: Homo sapiens

<400> SEQUENCE: 1

| | | | | | | |
|---|---|---|---|---|---|---|
| atgaccggct | ccgcggccga | cactcaccgc | tgcccccacc | ccaaaggcgc | caaaggcacc | 60 |
| cggtcccgga | gcagccacgc | gcggcccgtg | agcctcgcca | ccagcggggg | ctcagaggag | 120 |
| gaggacaaag | acggcggggt | gctgttccac | gtcaacaaga | gcggcttccc | catcgacagc | 180 |
| cacacctggg | agcgcatgtg | gatgcacgtg | gccaaggtgc | accctaaggg | gggagaaatg | 240 |
| gtgggcgcca | tcaggaacgc | cgccttcttg | gcaaagcctt | caataccccca | ggtcccaaac | 300 |
| tacaggctgt | cgatgacgat | cccagactgg | ctccaggcga | tccagaatta | catgaagacc | 360 |
| ctacaatata | atcacacagg | gacccagttc | tttgaaatta | ggaaaatgag | accgctgagt | 420 |
| gggttaatgg | aaacagcaaa | agaaatgacc | cgagagtcct | tgcctatcaa | atgccttgaa | 480 |
| gctgtcatcc | tgggcatcta | cttaaccaat | gggcagcctt | ccattgagcg | gttccccatc | 540 |
| agctttaaaa | cctacttctc | aggaaactac | tttcaccacg | ttgtgctggg | gatttactgc | 600 |
| aatggccgct | atggctcatt | gggcatgagc | cgcagggctg | agctgatgga | caagccattg | 660 |
| acttttcgga | ctctgagtga | cctcatcttt | gactttgagg | actcttacaa | gaaatacctg | 720 |
| cacacagtca | agaaggtcaa | gattgggctg | tacgtccccc | atgagcctca | tagcttccag | 780 |
| cccattgagt | ggaagcagct | ggtcctcaac | gtctcaaaga | tgctgagggc | tgacataagg | 840 |
| aaggagctgg | agaaatatgc | cagggacatg | agaatgaaga | tcctgaaacc | tgcaagtgcc | 900 |
| cactctccga | cccaagtgag | aagccgggga | aaatccctgt | ccccagaag | gagacaggca | 960 |
| agccccccga | ggaggctcgg | ccggcagagag | aagtcgcctg | cactgcctga | aaagaaggtg | 1020 |
| gctgatctga | gcactctgaa | tgaagtgggc | tatcaaatcc | gaatttag | | 1068 |

<210> SEQ ID NO 2
<211> LENGTH: 355
<212> TYPE: PRT
<213> ORGANISM: Homo sapiens

<400> SEQUENCE: 2

Met Thr Gly Ser Ala Ala Asp Thr His Arg Cys Pro His Pro Lys Gly
1               5                   10                  15

Ala Lys Gly Thr Arg Ser Arg Ser Ser His Ala Arg Pro Val Ser Leu
            20                  25                  30

Ala Thr Ser Gly Gly Ser Glu Glu Asp Lys Asp Gly Gly Val Leu
        35                  40                  45

Phe His Val Asn Lys Ser Gly Phe Pro Ile Asp Ser His Thr Trp Glu
    50                  55                  60

Arg Met Trp Met His Val Ala Lys Val His Pro Lys Gly Gly Glu Met
65                  70                  75                  80

Val Gly Ala Ile Arg Asn Ala Ala Phe Leu Ala Lys Pro Ser Ile Pro
                85                  90                  95

Gln Val Pro Asn Tyr Arg Leu Ser Met Thr Ile Pro Asp Trp Leu Gln
            100                 105                 110

Ala Ile Gln Asn Tyr Met Lys Thr Leu Gln Tyr Asn His Thr Gly Thr
        115                 120                 125

Gln Phe Phe Glu Ile Arg Lys Met Arg Pro Leu Ser Gly Leu Met Glu

-continued

```
                130                 135                 140
Thr Ala Lys Glu Met Thr Arg Glu Ser Leu Pro Ile Lys Cys Leu Glu
145                 150                 155                 160

Ala Val Ile Leu Gly Ile Tyr Leu Thr Asn Gly Gln Pro Ser Ile Glu
                165                 170                 175

Arg Phe Pro Ile Ser Phe Lys Thr Tyr Phe Ser Gly Asn Tyr Phe His
                180                 185                 190

His Val Val Leu Gly Ile Tyr Cys Asn Gly Arg Tyr Gly Ser Leu Gly
                195                 200                 205

Met Ser Arg Arg Ala Glu Leu Met Asp Lys Pro Leu Thr Phe Arg Thr
            210                 215                 220

Leu Ser Asp Leu Ile Phe Asp Phe Glu Asp Ser Tyr Lys Lys Tyr Leu
225                 230                 235                 240

His Thr Val Lys Lys Val Lys Ile Gly Leu Tyr Val Pro His Glu Pro
                245                 250                 255

His Ser Phe Gln Pro Ile Glu Trp Lys Gln Leu Val Leu Asn Val Ser
                260                 265                 270

Lys Met Leu Arg Ala Asp Ile Arg Lys Glu Leu Glu Lys Tyr Ala Arg
            275                 280                 285

Asp Met Arg Met Lys Ile Leu Lys Pro Ala Ser Ala His Ser Pro Thr
            290                 295                 300

Gln Val Arg Ser Arg Gly Lys Ser Leu Ser Pro Arg Arg Arg Gln Ala
305                 310                 315                 320

Ser Pro Pro Arg Arg Leu Gly Arg Arg Glu Lys Ser Pro Ala Leu Pro
                325                 330                 335

Glu Lys Lys Val Ala Asp Leu Ser Thr Leu Asn Glu Val Gly Tyr Gln
                340                 345                 350

Ile Arg Ile
        355
```